United States Patent [19]

Sottosanti

[11] Patent Number: 5,569,308
[45] Date of Patent: Oct. 29, 1996

[54] METHODS FOR USE IN BONE TISSUE REGENERATION

[76] Inventor: John S. Sottosanti, 2326 Calle Chiquita, La Jolla, Calif. 92037

[21] Appl. No.: 301,499

[22] Filed: Sep. 6, 1994

Related U.S. Application Data

[63] Continuation of Ser. No. 847,626, Mar. 6, 1992, Pat. No. 5,366,507.

[51] Int. Cl.$^6$ .................................... A61F 2/28; A61C 5/00
[52] U.S. Cl. ............................................ 623/165; 433/215
[58] Field of Search .................................. 623/16, 11, 66, 623/18; 424/422, 423, 424, 425, 426; 433/215, 217.1, 222.1

[56] References Cited

U.S. PATENT DOCUMENTS 4,619,655 10/1986 Hanker et al. ............................ 623/16

OTHER PUBLICATIONS

Caffesse, R. G., et al., "Response to An Absorbable Membrane for Guided Tissue Regeneration in Dogs." *J. Dent. Rest* 71 (Special Issue, AADR Abstracts) 71:297, 1534 (1992).
Caton, J, et al., "Synthetic Biodegradable Barrier for Regeneration in Human Periodontal Defects." *J. Dent. Res.* 69 (Special Issue, AADR Abstracts), 69: 275, 1335 (1990).
Choi, S. Y., et al., "Effect of a Collagen Matrix on Healing in Experimental Periodontal Wounds." *J. dent. Res* 71 (Special Issue, AADR Abstracts) 71 199, 1539 (1992).
Chung, K. M., et al., "Clinical Evaluation of a Biodegradable Collagen Membrane in Guided Tissue Regeneration." *J. Periodontol.* 61: 732–736 (1990).
Cortellini, P., et al., "Guided Tissue Regeneration with Different Materials." *Int. J. Periodont. Rest. Dent.* 10: 137–151 (1990).
Dyer, B., et al., "Guided Tissue Regeneration with Dentin Biomodification." *J. Dent. Res.* 71 (Special Issue, AADR Abstracts), 71: 297, 1533 (1992).
Gottlow, J., et al., "New Attachment Formation in the Monkey Using Guidor™, a Bioabsorbable GTR–Device." *J. Dent. Res.* 71 (Special Issue, AADR Abstracts), 71: 297, 1535 (1992b).
Gottlow, J., et al., "Clinical Result of GTR Therapy Using a Bioabsorbable Device (Guidor™)." *J. Dent. Res.* 71 (Special Issue, AADR Abstracts), 71: 199, 1537 (1992c).
Johns, L. P. et al., "Immunogenicity of a Bovine Collagen Membrane in Guided Tissue Regeneration (GTR)." *J. Dent. Res.* 71 (Special Issue, AADR Abstracts) 71: 199, 1533 (1992).
Kon, S., et al., "Regeneration of Periodontal Ligament Using Resorbable and Nonresorbable Membranes: Clinical, Histological, and Histometric Studty in Dogs." *Int. J. Periodont. Rest. Dent.* 11: 59–71 (1991).
Laurell, J., et al., "Gingival Response to Guidor™, a Bioabsorbable Device in GTR Therapy." *J. Dent. Res.* 71 (Special Issue, AADR Abstracts), 1536 (1992).

Magnusson, I., et al., "New Attachment Formation Following Controlled Tissue Regeneration Using Biodegradable Membranes." *J. Periodontal.* 59: 1–6 (1988).
Magnusson, I., et al., "Connective Tissue Repair in Circumferential Periodontal Defects in Dogs Following Use of a Biodegradable Membrane." *J. Clin. Periodontol.* 17: 243–248 (1990).
Nevins, M., et al., "Enhancement of the Damaged Edentulous Ridge to Receive Dental Implants: A Combination at Allograft and the Gore–Tex Membrane." *Int. J. Periodont. Rest. Dent.* 12:97–111 (1992).
Quinones, C. R., et al., "Evaluation of a Synthetic Biodegradable Barrier to Facilitate Guided Tissue Regeneration." *J. Dent. Res..* 69 (Special Issue, AADR Abstracts), 69: 275, 1336 (1990).
Quinones, C., et al., "Guided Tissue Regeneration Wound Healing Using a Synthetic Biodegradable Barrier in Interproximal Periodontal Defects." *J. Dent. Res.* 71 (Special Issue AADR Abstracts), 71: 297, 1532 (1992).
Nevins, M., et al., "A Comparative Study of the Effectiveness of e–PTFE Membranes With and Without Early Exposure During the Healing Period." *Int'l J. Periodontics & Restorative Dentistry*, vol. 14(2):97–111 (1994).
Simion, M., et al., "The Advantages Of Localized Ridge Augmentation Prior To Implant Placement: A Staged Event." *Int'l J. Periodontics & Restorative Dentistry*, vol. 14(2): 167–180 (1994).
Mellonig, *Int. J. Periodont. Rest. Dent.*, 6:41–55 (1984).
Lazzara, *Int. J. Periodont. Rest. Dent.*, 9:333–343 (1989).

*Primary Examiner*—Debra S. Brittingham
*Attorney, Agent, or Firm*—Steven J. Kirschner; Pretty, Schroeder, Brueggemann & Clark

[57] ABSTRACT

The present invention provides methods for use in bone tissue regeneration containing a barrier material and a graft material. The barrier material can be calcium sulfate, while the graft material can be any suitable material, including a composite graft material containing demineralized, freeze-dried, allogenic bone (DFDBA) and calcium sulfate. Alternatively, the barrier material can be any suitable material, while the graft material can be a composition of DFDBA and calcium sulfate.

31 Claims, No Drawings

METHODS FOR USE IN BONE TISSUE REGENERATION

This application is a continuation of application Ser. No. 07/847,626, filed Mar. 6, 1992, now U.S. Pat. No. 5,366,507.

BACKGROUND OF THE INVENTION

The present invention generally relates to compositions useful for therapeutic applications, and, more specifically, to compositions and methods of use of such compositions for bone tissue regeneration.

Bone tissue regeneration to repair bone defects, whether they are the result of injury, surgery, disease, or old-age, has been a common goal of medicine and dentistry. The procedure has seen more recent widespread application in the dental field due to the popularity of dental implants. Conventionally, bone tissue regeneration can be achieved by filling a bone defect site (recipient graft site) with graft material and covering the graft material with a barrier material to exclude competitive cells.

The nature of the graft material used determines how bone tissue is regenerated. If live active bone tissue is used as the graft material, it carries with it osteoblasts that form new bone. In addition, the live active bone tissue induces undifferentiated cells in the recipient graft site to differentiate into osteoblasts that further form new bone. Fresh autogenous cancellous bone and marrow is an example of live active bone tissue that can be used as a graft material. Demineralized, freeze-dried, allogenic bone ("DFDBA"), an inducing graft material, has also been used as a graft material. It induces undifferentiated cells in the graft site to differentiate into osteoblasts and grow into new bone, while the graft material is resorbed by the host. Finally, autogenous cortical bone chips, a scaffolding type graft material, has been used. The scaffolding type graft material passively attracts osteoblasts native to the recipient graft site in the scaffolding, where the cells may grow into new bone.

Although graft materials of the type that contain live active bone tissue produce excellent bone tissue regeneration, such materials require extraction of live tissue from a donor. If the donor is the same individual requiring bone tissue regeneration, such live tissue is in limited supply. Moreover, the remaining conventional graft materials do not always provide reliable bone tissue regeneration because they are not capable of inducing sufficient recipient graft site bone formation before competitive soft tissue and epithelial cells fill the recipient graft site.

The barrier material has functioned as a physical barrier to protect the graft material from disruption, to retard the ingrowth of unwanted tissue into the graft material and to allow cells to migrate into the recipient graft site from adjacent osseous tissues. To date the most popular barrier material has been a poly-tetrafluorethylene membrane (PTFE) even though there are many problems associated with its use. First, PTFE is not biodegradable. Therefore, it has been necessary to perform a second operation to remove the PTFE barrier. In addition, infection is likely to occur particularly if complete soft tissue coverage cannot be obtained. If the PTFE barrier is exposed, the patient can be uncomfortable until it is removed, sometime between four to six weeks. Since PTFE is generally used in a solid form and graft recipient sites have a variety of shapes and grooves, the PTFE barrier material must be trimmed during surgery to conform to the graft recipient site and then sutured in place. This procedure can be time consuming particularly if multiple defects exist.

Accordingly, a need exists for a composition that can be used to regenerate bone tissue in a reliable manner without undue risk of infection and without the need for prolonged and multiple operative procedures. The compositions of the present invention meet these needs and provides related advantages as well.

SUMMARY OF THE INVENTION

The present invention provides compositions containing barrier material and graft material that produce reliable bone tissue regeneration, while eliminating the need for prolonged and multiple surgical operations. The barrier material can be calcium sulfate, while the graft material can be any suitable material, including a composite graft material containing DFDBA and calcium sulfate. Alternatively, the barrier material can be any suitable material, while the graft material can be a composition of DFDBA and calcium sulfate. A kit can be assembled that contains calcium sulfate, a rehydrant and, optionally, DFDBA to prepare the compositions of the present invention.

The present invention also provides a novel composite graft material containing DFDBA and calcium sulfate. In a particular embodiment, the composite graft material contains about eighty percent DFDBA and about twenty percent calcium sulfate.

Finally, there is provided a method of enhancing guided tissue regeneration by filling a recipient graft site with graft material and covering the graft material with a barrier material. The barrier material can be calcium sulfate, while the graft material can be any suitable material, including the novel composite graft material of the present invention. Alternatively, the barrier material can be any suitable material, while the graft material is the novel composite graft material. Optionally, the barrier material can be covered with a protective material to prevent the barrier material from being dislodged or prematurely degraded.

Other features and advantages of the present invention will become apparent from the following detailed description of the invention which illustrates by way of example the principles of the invention.

DETAILED DESCRIPTION OF THE INVENTION

The present invention generally relates to compositions useful for therapeutic applications, and, more specifically, to compositions and methods of use of such compositions for bone tissue regeneration.

Bone tissue regeneration to repair bone defects, whether they are the result of injury, surgery, disease, or old-age, has been a common goal of medicine and dentistry, but has seen more recent widespread application in the dental setting due to the popularity of dental implants. Conventionally, bone tissue regeneration is achieved by filling a recipient graft site with graft material and covering the graft material with a barrier material. Over time, the graft material is resorbed by the host and new bone grows in place of the graft material.

The conventional graft materials currently in use, however, are either difficult to obtain or do not always provided reliable bone tissue regeneration because they are not capable of inducing sufficient bone formation in the recipient graft site before competitive soft tissue cells fill the site. Moreover, the barrier materials commonly in use are not biodegradable, necessitating a second entry into the graft recipient site to remove the barrier. The compositions of the present invention employ the conventional graft material/ barrier material layered scheme. However, the present compositions contain a novel composite graft material and/or a novel barrier material. The novel composite graft material facilitates reliable bone regeneration by inducing undifferentiated cells in the graft recipient site to become osteoblasts and from new bone (i.e., stimulating cellular transformation). The composite graft material also supplies a ready source of calcium for rapid mineralization. The novel barrier material is quick and easy to make and use during surgery and is completely biodegradable, eliminating the need for a second surgery to remove the barrier material.

In a particular embodiment of the present invention, a composition containing a barrier material and a graft material is provided. The barrier material can be calcium sulfate, while the graft material can be any suitable material known to one of skill in the art, including a composite graft material containing DFDBA and calcium sulfate. Alternatively, the barrier material can be any suitable material known to one of skill in the art, while the graft material can be a composition of DFDBA and calcium sulfate.

The barrier material is intended to perform the functions of protecting the graft material from disruption and retarding ingrowth of unwanted tissue into the graft material, while still allowing cells to migrate into the recipient graft site area from adjacent osseous tissue. Undesirable tissue that might grow into the graft material include, for example, epithelial and connective tissues. In an orthopedic setting, ingrowth of muscle tissue is also undesirable.

Suitable barrier materials for use in the present composition include, for example, poly-tetrafluorethylene, collagen, and polyglactin. A particularly useful barrier material is calcium sulfate, which can be conveniently prepared in a paste form immediately prior to its use by mixing calcium sulfate powder with any biocompatible, sterile liquid (rehydrant) known to those skilled in the art. Useful liquids for forming such a calcium sulfate paste include, for example, sterile water, sterile saline and sterile local anesthetic solution. Ideally, the calcium sulfate paste from which a calcium barrier can be formed is sufficiently dry enough to clump together as it is held on the end of the wax spatula, but sufficiently wet enough to spread with instruments when positioned onto the surfaces of the graft material.

A layer of calcium sulfate barrier material in a paste form can be easily spread over the graft material and shaped to conform to the confines of the recipient graft site. Thus, time in surgery is reduced because the need to trim the barrier material to conform to the graft recipient site is eliminated. In addition, as the calcium sulfate paste sets and hardens, it creates a solid physical barrier that is sufficiently dense to retard ingrowth of unwanted tissue, and yet porous enough to allow fluid exchange, ultimately reducing the risk of infection. Unlike other barrier materials commonly in use today, calcium sulfate is completely biocompatible and resorbable, thereby eliminating the need for a second operation to remove the barrier material once the bone tissue has regenerated.

The graft material is intended to function as a stimulus to bone tissue growth. It can directly supply bone forming cells, provide inducers of bone tissue growth, be a scaffolding-type structure that actively or passively attracts osteoblasts or provide any combination of these functions. Thus, the graft material may contain viable bone forming cells and also an inductive signal to cause recipient graft site cells to send bone forming cells to the site of bone regeneration.

Suitable graft materials for use in the present composition include, for example, autogenous cancellous bone, DFDBA, autogenous cortical bone chips, and hydroxylapatite. A particularly useful graft material includes a composite of DFDBA and calcium sulfate. Inclusion of DFDBA in the composite graft material actually induces new bone formation by stimulating cellular transformation. At the same time, the calcium sulfate in the graft material composition provides the benefit of enhanced binding of the DFDBA to an osseous recipient graft site and enhanced mineralization by providing a ready source of calcium ions. Although it is contemplated that a useful composite graft material can be obtained by mixing DFDBA and calcium sulfate so that the composition can contain these reagents in a range of 50% DFDBA, 50% calcium sulfate to 90% DFDBA, 10% calcium sulfate. Preferably, the composite graft material contains about 80% DFDBA and 20% calcium sulfate.

The present invention further provides a novel composite graft material containing DFDBA and calcium sulfate for use in bone tissue regeneration. As discussed above, useful composite graft material can be obtained from a range DFDBA and calcium sulfate mixtures. Preferably, the composite graft material would contain about eighty percent DFDBA and about twenty percent calcium sulfate.

The composite graft material can be conveniently prepared, for example, by first rehydrating DFDBA powder with any biocompatible, sterile liquid rehydrant conventionally used for dental or medical applications. Preparation of the composite graft material is preferably started by rehydrating DFDBA powder at least ten minutes before the composite graft material is to be used. The rehydrated DFDBA mixture is then mixed with calcium sulfate into the rehydrated DFDBA just prior to use. A calcium sulfate powder can, for example, be added to the rehydrated DFDBA until it amounts to about 20 percent of the total powder mixture. Additional rehydrant can be added until the entire composition graft material is moistened. Useful rehydrants include, for example, sterile water, sterile saline and sterile, local anesthetic solution.

In yet another embodiment of the present invention, there is provided a kit containing an effective amount of calcium sulfate and, optionally, DFDBA to prepare the composition or composite graft material of the present invention. For example, kits can be assembled that contain sealed packages of sterile DFDBA and sterile calcium sulfate. In addition, ancillary reagents can be included, for example sterile rehydrants and the like.

The present invention further provides a method of regenerating bone tissue by filling a recipient graft site with graft material and placing a layer of barrier material over at least a portion of the graft material. The recipient site should be completely covered or filled with suitable graft material or overfilled if soft tissue coverage can be obtained. Once the recipient site is covered or filled, the barrier material should be laid over the graft material. The barrier material should cover at least a portion of the graft material and can extend to the tissue surrounding the graft recipient site.

For use in the present methods, the barrier material can be calcium sulfate, while the graft material can be any suitable material known to one of skill in the art, including a composite graft material containing DFDBA and calcium sulfate. Alternatively, the barrier material can be any suitable material known to one of skill in the art, while the graft material can be a composition of DFDBA and calcium sulfate.

Suitable graft materials for use in the present composition include, for example, autogenous cancellous bone, DFDBA, autogenous cortical bone chips, and hydroxylapatite. As discussed above, a particularly useful graft material includes a composition of DFDBA and calcium sulfate, preferably containing about eighty percent DFDBA and twenty percent calcium sulfate.

Suitable barrier materials for use in the methods include, for example, poly-tetrafluoroethylene, polyglactin and calcium sulfate. Calcium sulfate is the preferred barrier material because, as discussed above, it is biodegradable and easy to use. Because calcium sulfate barrier material will degrade and be absorbed by its host as the bone tissue regenerates, the amount of calcium sulfate barrier material to be applied is dependent upon the amount of graft material used and is directly related to the amount of time necessary to regenerate bone tissue. Thus, the applied thickness of calcium sulfate barrier material should increase with the amount of graft material used. For example, if the graft recipient site contains a layer of graft material of up to 5 mm thick, then the calcium sulfate barrier material is preferably between 1.5 and 2 mm thick.

If an orthopedic or dental implant is placed into a graft recipient site, the implant should first be secured in the graft recipient site and then the graft material should be packed around the implant. Barrier material can then be placed over the graft material and implant, or around the implant and over the graft material.

Optionally, the barrier material can be covered with a protective material to prevent dislodging of the barrier material or premature degradation of the barrier material. For example, if the graft recipient site is bone in the jaw of a mouth, the barrier material should be covered by suturing surrounding epithelial and connective tissue. Elsewhere in a body, surrounding muscle tissue can also be used as a protective material. If total soft tissue coverage is not possible, a dressing can be used as a protective material to cover the barrier material.

The following examples are intended to illustrate but not limit the invention.

EXAMPLE I

Materials

Demineralized, freeze-dried, human, allogenic, cortical bone powder in particle size of 300 to 700 microns was obtained from tissue banks accredited by the American Association of Tissue Banks. Certified pure calcium sulfate obtained from U.S. Gypsum, Inc. (Chicago, Ill.) was sterilized in a dry heat oven at 325° F. for 1.5 hours and then stored in sterile jars until surgery.

EXAMPLE II

Preparation of Composite Graft Material

At least ten minutes prior to filling the graft recipient site with composite graft material, DFDBA was emptied into a sterile dappen dish and rehydrated with sterile water. Immediately prior to filling the graft recipient site with composite graft material, sterile calcium sulfate powder was added to the rehydrated DFDBA so that the calcium sulfate comprised about twenty percent of the total composition. The composition was stirred with a #7 wax spatula until the mix was homogeneous, and then additional sterile water was added until the entire composition was moistened.

EXAMPLE III

Preparation of Calcium Sulfate Barrier Material

After the recipient graft site was filled with composite graft material, the calcium sulfate barrier material was prepared as a paste in a dappen dish by mixing sterile water into sterile calcium sulfate powder. Sterile water was added to the sterile calcium sulfate powder until the mixture clumped together on the end of a spatula, but was still wet enough to spread.

EXAMPLE IV

Case Study A

A seventy-two year old male in good health had a mandibular cuspid with a facial trough-like defect extending from the distal to the facial and ending on the mesial. The base of the defect on the facial extended to within several millimeters of the apex. Heavy calculus was present and it extended into the infrabony areas of the cementum.

To fully remove the calculus, the cementum had to removed in conformity with acceptable dental techniques. The surface was smoothed by use of ultrasonic scalers and rotary root planing burs and treated with citric acid, pH 1 for two to three minutes. The infrabony defect, the graft recipient site, was filled with a composite graft material prepared in accordance with Example II.

A 1.5 to 2 millimeter thick layer of calcium sulfate barrier material, prepared in accordance with Example III was placed over the composite graft material in the shape of an apron. The calcium sulfate barrier material adhered circumferentially to the cuspid as well as the proximal root surfaces of the adjacent teeth. It was not necessary to keep the calcium sulfate away from the vertical incisions.

Surrounding epithelial and connective tissues were sutured to cover the calcium sulfate barrier material. A dental dressing was secured over the graft recipient site.

The graft recipient site was re-entered after three months for re-contouring the bone and placement of a free gingival graft. Bone filled the entire trough and considerable supracrestal bone was present on the disto-facial aspect of the cuspid root.

EXAMPLE V

Case Study B

A healthy fifty-two year old female had severe periodontal pockets with extensive bone loss on the distal of the mandibular right first bicuspid and the distal of the mandibular left second molar. The defects were curretted, root debridement was performed, and the dental root surfaces were treated with citric acid, pH 1 for two to three minutes.

The recipient graft sites were filled with composite graft material prepared in accordance with Example II. A 1.5 to 2 millimeter thick layer of calcium sulfate barrier material, prepared according to Example III was placed over the composite graft material and extended onto surrounding tissue for an additional two to three millimeters. Surrounding epithelial and connective tissues were sutured to cover the calcium sulfate barrier material. A dental dressing was secured over the graft recipient site.

Antibiotic therapy was instituted to prevent infection and the patient was seen weekly for four weeks. Subsequently the teeth were scaled and the patient placed into three month scaling program. Pocket depths remained shallow and radiographs taken at two years showed complete bone tissue regeneration.

EXAMPLE VI

Case Study C

A seventy-eight year old man on anticoagulant therapy suffered from a root fracture of his mandibular right first bicuspid necessitating its extraction. It was decided that an endosseous implant had to be immediately placed into the extraction socket. There was a facial dehiscence resulting in approximately four millimeters of implant exposure.

Composite graft material prepared according to Example III was packed around the implant, filling-in the dehiscence and extending in a coronal direction to a level near the top of the cover screw.

Although the anticoagulant therapy was stopped several days before the surgery, it was anticipated that there would still be sufficient hemorrhaging to risk mixture of blood with the calcium sulfate barrier material. Therefore, at the beginning of the operation calcium sulfate barrier material was prepared as set forth in Example III and allowed to harden. After the recipient graft site was filled with composite graft material, the hardened calcium sulfate barrier material was ground into small particles using the end of a dental instrument. A small amount of these particles (10% by volume) was added to sterile, calcium sulfate powder in a dappen dish. Sterile water was then added until the mixture clumped together on the end of a wax spatula, but was still wet enough to spread. This special technique for preparing the calcium sulfate barrier material was performed to accelerate its setting time.

A 1.5 to 2 millimeter thick layer of calcium sulfate barrier material was then spread over the composite graft material and implant, extending two to three millimeters onto surrounding tissue. Surrounding epithelial and connective tissues were sutured to cover the calcium sulfate barrier material and a dental dressing was secured over the graft recipient site.

When the graft recipient site was re-entered after three months to uncover the implant, the implant was buried in bone with only a small section of the cover screw exposed. Osseous contouring of the new bone revealed a bone which was dense and vascular and appeared to be clinically healthy and mature.

EXAMPLE VII

Case Study D

A twenty-three year old female fell from her bicycle and fractured her left maxillary central incisor. The root sustained several vertical fractures resulting in a sinus tract which obliterated the entire facial plate of bone. The restorative dentist cut off the clinical crown at the height of the gingival margin, made a chair-side three unit temporary bridge.

A facial flap was elevated and the root was easily removed with elevators and a hemostat. Composite graft material prepared as set forth above in Example II and packed into the socket and against the palatal wall of the socket until an ideal facial plate of bone was constructed.

Calcium sulfate barrier material, prepared as set forth above in Example III was used to completely cover, on both its facial and incisal aspects, the facial plate bone constructed from composite graft material. To cover the calcium sulfate barrier material, surrounding epithelial and connective tissues were sutured and a temporary bridge was seated so that the apical extent of the pontic pressed against the incisal surface of the barrier and helped protect the barrier material.

Healing proceeded rapidly without signs of inflammation. At three weeks the facial tissue was still seen juxtaposed against the facial and apical extent of the pontic. This procedure can be used when multiple teeth need to be preserved for the future placement of implants.

Although the invention has been described with reference to the presently-preferred embodiments, it should be understood that various modifications can be made without departing from the spirit of the invention. Accordingly, the invention is limited only by the following claims.

I claim:

1. A method of regenerating bone tissue, comprising:
   (a) filling a recipient graft site with graft material, the graft material comprising a stimulus to bone tissue growth,
      wherein the stimulus to bone tissue growth is selected from the group consisting of a bone forming cell, an inducer of bone tissue growth, a scaffolding-type structure that actively attracts osteoblasts, a scaffolding-type structure that passively attracts osteoblasts, and a combination of any of these; and
   (b) placing a layer of resorbable barrier material over at least a portion of the graft material,
      wherein the barrier material comprises calcium sulfate, and
      wherein the barrier material physically protects the graft material, retards the ingrowth of unwanted tissue into the graft material, and allows cells to migrate into the recipient graft site from adjacent osseous tissue.

2. The method of claim 1, wherein the barrier material further comprises rehydrant.

3. The method of claim 1, wherein the barrier material is substantially free from calcium phosphate ceramic particles.

4. The method of claim 1, wherein the barrier material is pre-set.

5. The method of claim 1, wherein the barrier material is in a paste form.

6. The method of claim 1, further comprising covering the layer of barrier material with a protective material.

7. The method of claim 1, wherein the graft material comprises demineralized, freeze-dried allogenic bone (DFDBA) and calcium sulfate.

8. The method of claim 7, wherein the graft material comprises about eighty percent DFDBA and about twenty percent calcium sulfate.

9. The method of claim 8, further comprising covering the layer of barrier material with a protective material.

10. The method of claim 1, wherein the barrier material consists essentially of calcium sulfate.

11. The method of claim 10, wherein the barrier material is pre-set.

12. The method of claim 10, wherein the barrier material is in a paste form.

13. The method of claim 10, wherein the graft material comprises demineralized, freeze-dried allogenic bone (DFDBA) and calcium sulfate.

14. The method of claim 13, wherein the graft material comprises about eighty percent DFDBA and about twenty percent calcium sulfate.

15. The method of claim 14, further comprising the step of covering the layer of barrier material with a protective material.

16. A method in accordance with claim 10, wherein the barrier material creates a solid physical barrier that is sufficiently dense to retard ingrowth of unwanted tissue, and yet porous enough to allow fluid exchange.

17. A method in accordance with claim 1, wherein the stimulus to bone growth is a bone forming cell.

18. A method in accordance with claim 17, wherein the barrier material consists essentially of calcium sulfate.

19. A method in accordance with claim 1, wherein the stimulus to bone growth is an inducer of bone tissue growth.

20. A method in accordance with claim 19, wherein the barrier material consists essentially of calcium sulfate.

21. A method in accordance with claim 1, wherein the stimulus to bone growth is a scaffolding-type structure that actively attracts osteoblasts.

22. A method in accordance with claim 21, wherein the barrier material consists essentially of calcium sulfate.

23. A method in accordance with claim 1, wherein the stimulus to bone growth is a scaffolding-type structure that passively attracts osteoblasts.

24. A method in accordance with claim 23, wherein the barrier material consists essentially of calcium sulfate.

25. A method in accordance with claim 1, wherein the barrier material creates a solid physical barrier that is sufficiently dense to retard ingrowth of unwanted tissue, and yet porous enough to allow fluid exchange.

26. A method of regenerating bone tissue, comprising:
(a) filling a recipient graft site with graft material, the graft material comprising a stimulus to bone tissue growth,
wherein the stimulus to bone tissue growth is selected from the group consisting of a bone forming cell, an inducer of bone tissue growth, a scaffolding-type structure that actively attracts osteoblasts, a scaffolding-type structure that passively attracts osteoblasts, and a combination of any of these; and
(b) placing a layer of resorbable barrier material over at least a portion of the graft material,
wherein the barrier material consists essentially of calcium sulfate, and
wherein the barrier material physically protects the graft material.

27. A method in accordance with claim 26, wherein the barrier material creates a solid physical barrier that is sufficiently dense to retard ingrowth of unwanted tissue, and yet porous enough to allow fluid exchange.

28. A method of regenerating bone tissue, comprising:
(a) filling a recipient graft site with graft material, the graft material comprising a stimulus to bone tissue growth,
wherein the stimulus to bone tissue growth is selected from the group consisting of a bone forming cell, an inducer of bone tissue growth, a scaffolding-type structure that actively attracts osteoblasts, a scaffolding-type structure that passively attracts osteoblasts, and a combination of any of these; and
(b) placing a layer of resorbable barrier material over at least a portion of the graft material,
wherein the barrier material consists essentially of calcium sulfate, and
wherein the barrier material retards the ingrowth of unwanted tissue into the graft material.

29. A method in accordance with claim 28, wherein the barrier material creates a solid physical barrier that is sufficiently dense to retard ingrowth of unwanted tissue, and yet porous enough to allow fluid exchange.

30. A method of regenerating bone tissue, comprising:
(a) filling a recipient graft site with graft material, the graft material comprising a stimulus to bone tissue growth,
wherein the stimulus to bone tissue growth is selected from the group consisting of a bone forming cell, an inducer of bone tissue growth, a scaffolding-type structure that actively attracts osteoblasts, a scaffolding-type structure that passively attracts osteoblasts, and a combination of any of these; and
(b) placing a layer of resorbable barrier material over at least a portion of the graft material,
wherein the barrier material consists essentially of calcium sulfate, and
wherein the barrier material allows cells to migrate into the recipient graft site from adjacent osseous tissue.

31. A method in accordance with claim 30, wherein the barrier material creates a solid physical barrier that is sufficiently dense to retard ingrowth of unwanted tissue, and yet porous enough to allow fluid exchange.

* * * * *